US00PP08963P

United States Patent [19]

Vaughn

[11] Patent Number: Plant 8,963

[45] Date of Patent: Oct. 25, 1994

[54] BERMUDA GRASS 'VAUGHN'S #1'

[76] Inventor: Terrell Vaughn, Rte. 1, Box 231, Walling, Tenn. 38587

[21] Appl. No.: 82,923

[22] Filed: Jun. 25, 1993

[51] Int. Cl.[5] ..... A01H 5/00

[52] U.S. Cl. ..... Plt./90

[58] Field of Search ..... Plt. 90

*Primary Examiner*—James R. Feyrer

*Attorney, Agent, or Firm*—Klarquist Sparkman Campbell Leigh & Whinston

[57] ABSTRACT

A new variety of Bermuda grass characterized by its tall-growth, winter hardiness, vigorous rooting, excellent feed quality and resistance to helminthosporium leaf spot.

2 Drawing Sheets

DESCRIPTION

The present invention relates to a new and distinct variety of Bermuda grass, which I have named 'Vaughn's #1'.

My attention was first directed to 'Vaughn's #1' variety because of its characteristic for tall growth. I first recognized this variety as distinct as it was growing in a cultivated area on a farm in White County, Tenn. The cultivated field from which I first selected my new variety had been sown in common Bermuda grass for about 100 years, and I previously had noticed some tall growing native common Bermuda grass that grew to approximately 18 inches tall. The nvew variety was significantly taller. I believe that the Bermuda grass I had sowed and the tall native grass that was already present on the field cross-pollinated and produced tha new hybrid Bermuda grass, 'Vaughn's #1, that I selected.

I have observed my new variety for a number of years growing in cultivated areas on my farm in White County, Tenn. My observations have confirmed that my variety is a distinct and unusual cultivar. Subsequent asexual propagation of my variety by vegetative cuttings under my directions, and observation of the resulting progeny has proven the characteristics of my new variety to be fixed. Furthermore, these observations have confirmed that my new variety represents a new and improved variety of Bermuda grass, as particularly evidenced by the following unique combination of characteristics, which have proven firmly fixed, are outstanding therein, and which distinguish it from all of the varieties of this species of which I am aware:

1. Tall-growing;
2. Winter hardiness;
3. Vigorous rooting;
4. Excellent feed quality; and
5. Resistance to brown leaf spot (Helminthosporium).

The accompanying photographs depict the color of the foliage of my new variety, as well as the shape of the plant and the size thereof, as nearly true as is reasonably possible to make the same in a color illustration of this character.

Figure 1:
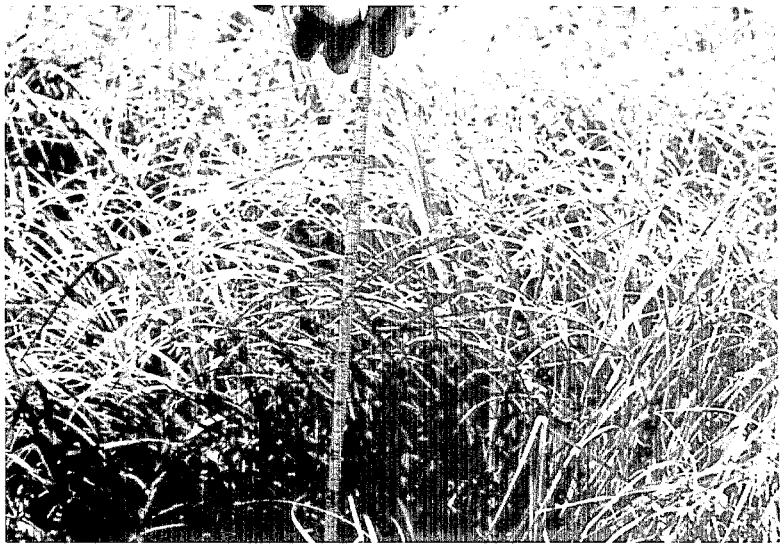
FIG. 1 is a color photograph ov the Bermuda grass of the present invention.
Figure 2:
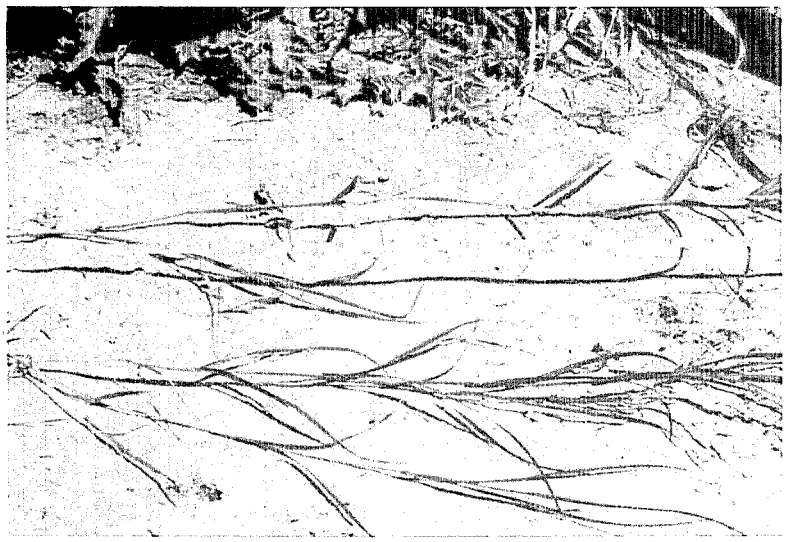
FIG. 2 is a color photograph of the Bermuda grass of the present invention, showing its characteristic tail growth.
Figure 3:
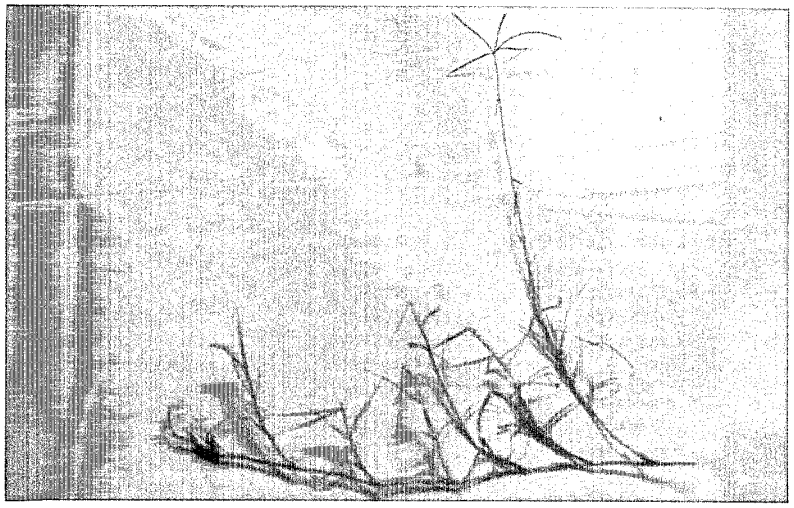
FIG. 3 is a color photograph of the bermuda grass of the present invention, showing its reproductive parts.
Figure 4:
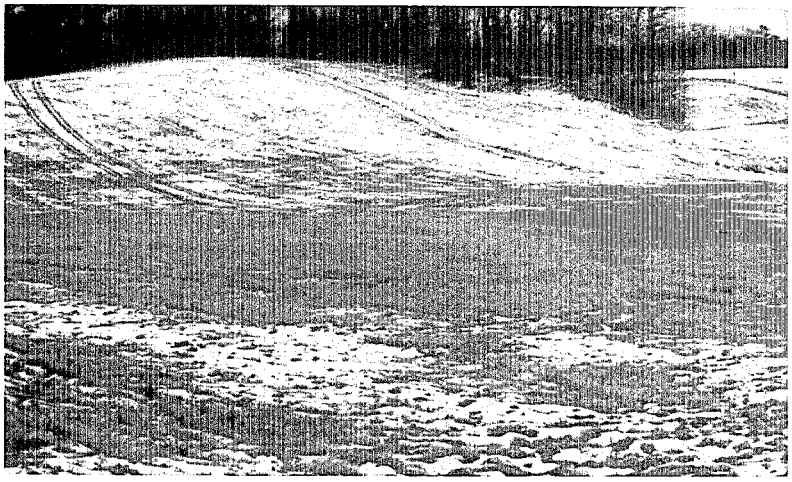
FIG. 4 is a color photograph of a field of the bermuda grass of the present invention taken of Jan. 23, 1993 after a hard freeze with night time temperatures on consective nights of 6° F. below zero, 2° F., 10° F. for two nights, 12° Fl for two nights and several other nights with below freezing temperatures.

FIG. is a color photograph of the bermuda grass of the present invention, showing its mature stolens maintaining their green color after the freeze depicted into FIG. 4.

My new variety of Bermuda gass differs from the parent cultivars in a number of respects. As previously noted, the characteristic that first drew my attention to my new variety was its tall-growing qualities. The new hybrid reaches more than 20 inches in height before beginning to squat. in comparison, I am familiar with native tall-growing common Bermuda grass that grew to approximately 18 inches tall before beginning to squat, but nothing I had seen before reached the height of the new 'Vaughn's #1'.

Another characteristic of the new variety is its winter hardiness. Observatin of 'Vaughn's #1' has shown that it survives temperatures as low as −20° F., and extended periods of single digit fahrenheit temperatures that have killed most Sourthern Magnolias and boxwoods living in the same geographic area. Further evidence of the winter hardines of the new variety is shown by the survivability of young roots of newly planted vegetative cuttings. I have made plantings of the vegetative cuttings over two different years around the first of September, and the young roots, in each case, have survived the winter.

During the 1992/1993 winter, the 'Vaughn's #1' variety had green sprouts in winter. A colder February and a mid-March blizzard in the White County, Tenn. area killed the sprouts back. However, ten days after the snow cleared, new green sprouts occurred and 'Vaughn's #1'was ready to mow for hay by the last week of may, being more than 18 inches tall.

The new hybrid has also proved to be a very rigorous rooter from vegetative cuttings disked into the soil. The cuttings being growing within one week. I have observed runners growing at the rate of 2 inches per day, only two weeks after planting. Plantings made on the first of July and on the first of August established a complete cover before first frost.

Another characteristic of the new variety is its excellent feed quality. 'Vaughn's #1' has tested low in fiber, with total dietary nitrogen on three tests ranging from 60 to 54. Protein content ranged from 15.44 to 17.22 percent, varying with different cuttings and fertilization. Analysis of several characteristics of the new variety is provided below in Table 1. These analyses were preformed by the Co-Op lab in La Verne, Tenn.

TABLE 1

| Date of Analysis | Moisture (%) | Crude Protein (Dry Basis)(%) | Acid Detergent Fiber (Dry)(%) |
|---|---|---|---|
| 7/27/92 | 24.50 | 17.22 | 34.58 |
| 10/9/92[a] | NR* | 16.94 | 34.36 |
| 10/9/92[b] | NR* | 15.44 | 37.15 |

*Not Recorded

[a]Top dressed after last cutting with nitrogen. Approximately 230 lbs. total nitrogen per acre for the season.

[b]No top dressing. Approximately 130 lbs. total nitrogen per acre added early in the season.

I have observed the new variety left standing in the fall that showed a lack of woody, fibrous texture compared with common Bermuda grass. Calves fed on the new variety hybrid have shown excellent growth and condition.

I have observed that the new variety is, for the most part, non-flowering, and most reproduction is vegetative. However, under certain conditions I have observed flowering of Vaughn's #1. Thus, I have observed flowering at the edges of a field planted in Vaughn's #1 where there is little or no fertilizer and the grass is not cut at the regular mowing times. I have also observed flowering on Vaughn's #1 planted on red clay soil that has low content of organic matter in the soil, and where growth is slower from low fertilizer or drought stress.

As a further example, I have observed that the flowering seems to occur only where the ground is not completely shaded by the grass. Even where the grass is not mowed but has a heavy growth coverig on the ground, no flowering has been observed. The flowering characteristic was more noticeable this year (1993) due to a failure to distribute fertilizer evenly over the entire field. On portions of the field that were fertilized properly, no flowering was observed.

Finally, the new variety has good resistance to brown leaf spot (helminthosporium).

The coloring of the new variety is similar to the common varieties of bermuda grass that grow in White County, Tenn., except for the flowering parts, which as noted rarely occur. The seed head is a pale green with almost white underneath where the seed pods are located. In contrast, the seed heads of common bermuda grass are generally a rust color to reddish in color.

Figure 5:
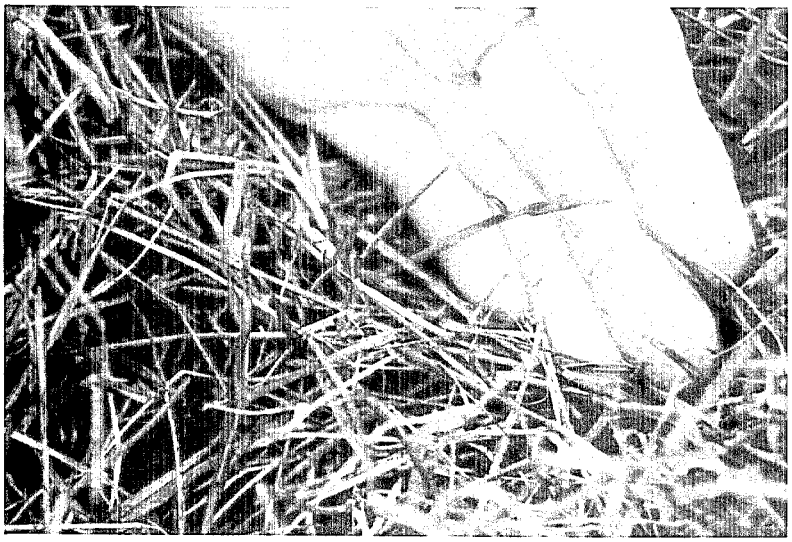

The new variety is very cold tolerant and does not become dormant until a hard freeze with temperatures below 28° F. In mid winters when temperatures remain above 15° F., green stolens can be found throughout the winter. The mature stolens maintain their green color above the ground throughout the winter and are not killed back to ground level, as shown in FIG. 5. New stolen sprouts are therefore ready to begin growth early in the spring, as soon as the night time temperatures remain above freezing. I observed in March, 1993, that there were 1 to 2 inch stolens on the new variety within ten days after the snow from a blizzard had melted off. Also in 1993, there was a late freeze in April with temperatures in the mid twenties degree Fahrenheit. This late freeze killed back some of the 6 inch growth, but the field was ready to cut for hay by May 25, 1993. This was earlier than a large percentage of the fescure fields were cut in this area.

Productivity of the new variety is increased over previously known varieties. A ten acre hay field was mowed four times in 1993 without a variance by more than two rolls in any of the four cuttings. Since the fall of 1993 was very dry, the continued productivity of the new variety under drought conditions is evidence of the drought tolerance of this variety. In addition, the quality is also maintained in the fall. The last cuttings in 1992, which occurred during the last week of Septemer, tested 16.94% crude protein and about 64% T.B.N.

The spread of the new variety from stolens distinguishes this variety from other known varieties. I reproduced this variety from vegetative cuttings. Such reproduction has been done under good conditions such as proper soil preparation on good soil and with timely rainfall, and also under poor conditions with poor soil preparation on poor soils with lack of rainfall. Each of the plantings has been successful, whether under good conditions or poor conditions. With one of the plantings in Jun. 1992, the growth of the stolens was measured 15 days after planting the clippings and they were growing at the rate of 2 inches per 24 hours. One of The plantings in Jun. 1993 on a ten acre parcel produced a hay crop of 3.6 big rolls per acre on Aug. 1. this planting was then pastured for six weeks.

On one of the trails with poor soil and poor preparation with delayed rainfall, the field was disked a pond down and the clippings were spread the same day because of predicted rainfall. nonetheless, full coverage was obtained by the fall.

The sod appears to thicken from rhizome growth. The new variety spreads with great vigor from stolens. The rhizomes are close to the crown and thick in the sod. Higher productivity rates apparently are due to dense sod and rapid growth with a full cutting of 18 to 20 inches produced within 26 to 36 days.

Thatching requirements do not seem to be applicable to the new variety that would be regularly mowed and raked with removal of growth for hay.

BOTANICAL DESCRIPTION

The following is a detailed description of my new variety of Bermuda grass, *Cynodon dactylon* 'Vaughn's #1', with color terminology in accordance with The Royal Horticultural Colour Chart (hereinafter "R.H.S.) published by The Royal Horticultural Society of London.

Parentage: Unknown.

Propagation: Holds to distinguishing characteristics through succeeding propagation by vegetative cuttings.

Locality where grown and observed: White County, Tenn.

Growth habit: *Cynodon dactylon* 'Vaughn's #1' is a warm-season, stoloniferous and rhizomatous perennial. It branches from basal nodes as well as from buds produced at some upper nodes.

Culm: Glabrous, rounded, solid, 48 to 60 cm in length with 7 to 11 nodes.

Average node diameter: 2.3 mm.

Internode diameter: 2.0 mm.

Average internode length: 7.5 cm

Leaf blade: Folded, 13 to 18 cm long, upright, uniform color from midrib to margin, average 4 mm wide.
Sheath: Open, shorter than internode, 5.5 to 6.5 cm in length.
Ligule: A conspicuous ring of white hairs.
Auricle: Rounded, not prominent.
Spikelet: None produced.
Color: Variable; similar to 141B to 173D depending upon conditions.

COMPARISON WITH OTHER BERMUDA GRASSES

'Vaughn's #1' hybrid Bermuda grass is more winter hardy than othe rhybrids; more resistant to helminthosporium leaf spot; has excellent vigorous growth; has a low fiber content and high palatability, and as a result cattle eat it well and maintains quality through fall when other varieties' quality and palatability goes down.

I claim:

1. A new and distinct variety of Bermuda grass substantially as herein shown and described, characterized particularly as to novelty by its tall-growing characteristic, tis winter hardiness, its very vigorous rooting; its excellent feed quality; and resistance to helminthosporium leaf spot.

* * * * *

UNITED STATES PATENT AND TRADEMARK OFFICE

CERTIFICATE OF CORRECTION

PATENT NO. : PP 8,963

DATED : October 25, 1994

INVENTOR(S) : Terrell Vaughn

It is certified that error appears in the above-indentified patent and that said Letters Patent is hereby corrected as shown below:

Column 1, line 14, "nvew" should read —new—.
Column 1, line 17, "tha" should read —the—.
Column 1, line 46, "ov" should read —of—.
Column 1, line 49, "tail" should read —tall—.
Column 2, line 4, "of" should read —on—. (second occurrence)
Column 2, line 7, "12°Fl" should read —12°F—.
Column 2, line 11, "FIG. is" should read —FIG. 5 is—.
Column 2, line 14, "gass" should read —grass—.
Column 2, line 19, "in comparison" should read —In comparison—.
Column 2, line 25, "Observatin" should read —Observation—.
Column 2, line 30, "hardines" should read —hardiness—
Column 2, line 42, "#1'was" should read —#1 was—.
Column 2, line 43, "may should read —May—.
Column 2, line 45, "being" should read —begin—.
Column 3, line 4, "54" should read —64—.
Column 3, line 39, "coverig" should read —covering—.
Column 4, line 2, "Fescure" should read —Fescue—.
Column 4, line 33, "nonetheless" should read —Nonetheless—.
Column 5, line 14, "othe rhybrids" should read —other hybrids—.
Column 6, line 10, "tis' should read —its—.

Signed and Sealed this

Twenty-first Day of March, 1995

*Attest:*

Bruce Lehman

BRUCE LEHMAN

*Attesting Officer*

*Commissioner of Patents and Trademarks*